United States Patent
Dang et al.

(10) Patent No.: US 6,758,859 B1
(45) Date of Patent: Jul. 6, 2004

(54) INCREASED DRUG-LOADING AND REDUCED STRESS DRUG DELIVERY DEVICE

(76) Inventors: Kenny L. Dang, 2872 Hemlock Ave., San Jose, CA (US) 95128; Nazanine Matin, 3155 Loma Verde Pl., Palo Alto, CA (US) 94303; Henjen Ho, 860 Hillwood Dr., San Jose, CA (US) 95129

( * ) Notice: Subject to any disclaimer, the term of this patent is extended or adjusted under 35 U.S.C. 154(b) by 45 days.

(21) Appl. No.: 09/699,786

(22) Filed: Oct. 30, 2000

(51) Int. Cl.$^7$ .................................................. A61F 2/06
(52) U.S. Cl. ........................................ 623/1.15; 623/1.42
(58) Field of Search ........................... 623/1.42, 1.43, 623/1.45, 1.15, 1.16, 1.36, 1.39, 1.4

(56) References Cited

U.S. PATENT DOCUMENTS

| | | | |
|---|---|---|---|
| 4,459,252 A | 7/1984 | MacGregor | 264/46.9 |
| 5,059,211 A | 10/1991 | Stack et al. | 606/198 |
| 5,163,952 A | 11/1992 | Froix | 623/1 |
| 5,306,286 A | 4/1994 | Stack et al. | 606/198 |
| 5,514,154 A | 5/1996 | Lau et al. | 606/195 |
| 5,527,337 A | 6/1996 | Stack et al. | 606/198 |
| 5,569,295 A | 10/1996 | Lam | 606/198 |
| 5,603,721 A | 2/1997 | Lau et al. | 606/195 |
| 5,700,286 A | 12/1997 | Tartaglia et al. | 623/1 |
| 5,713,949 A | 2/1998 | Jayaraman | 623/1 |
| 5,766,710 A | 6/1998 | Turnlund et al. | 428/36.1 |
| 5,769,883 A | 6/1998 | Buscemi et al. | 623/1 |
| 5,843,172 A | 12/1998 | Yan | 623/1 |
| 5,855,600 A * | 1/1999 | Alt | 606/195 |
| 5,873,904 A | 2/1999 | Ragheb et al. | 623/1 |
| 5,891,108 A | 4/1999 | Leone et al. | 604/264 |
| 5,972,027 A * | 10/1999 | Johnson | 424/422 |
| 6,071,305 A | 6/2000 | Brown et al. | 623/1 |
| 6,120,536 A | 9/2000 | Ding et al. | 623/1.43 |
| 6,120,847 A | 9/2000 | Yang et al. | 427/335 |
| 6,129,755 A * | 10/2000 | Mathis et al. | 623/1.15 |
| 6,171,334 B1 * | 1/2001 | Cox | 623/1.15 |
| 6,203,569 B1 | 3/2001 | Wijay | 623/1.15 |
| 6,206,915 B1 | 3/2001 | Fagan et al. | 623/1.42 |
| 6,254,632 B1 * | 7/2001 | Wu et al. | 623/1.15 |
| 6,273,908 B1 * | 8/2001 | Ndondo-Lay | 606/194 |
| 6,273,910 B1 * | 8/2001 | Limon | 623/1.15 |
| 6,273,913 B1 | 8/2001 | Wright et al. | 623/1.42 |
| 6,287,628 B1 | 9/2001 | Hossainy et al. | 427/2.3 |
| 6,299,604 B1 * | 10/2001 | Ragheb et al. | 604/265 |
| 6,334,871 B1 * | 1/2002 | Dor et al. | 623/1.34 |
| 6,379,381 B1 | 4/2002 | Hossainy et al. | 623/1.42 |
| 6,395,326 B1 | 5/2002 | Castro et al. | 427/2.24 |
| 6,416,543 B1 | 7/2002 | Hilaire et al. | 623/1.16 |
| 6,506,437 B1 | 1/2003 | Harish et al. | 427/2.25 |
| 6,562,065 B1 * | 5/2003 | Shanley | 623/1.15 |

FOREIGN PATENT DOCUMENTS

| | | |
|---|---|---|
| EP | 0875218 | 11/1998 |
| EP | 0850651 | 8/2000 |
| JP | 11-299901 | 11/2002 |
| WO | 90/01969 | 3/1990 |
| WO | 98/23228 | 6/1998 |
| WO | 99/16386 | 4/1999 |
| WO | WO 01/00112 | 1/2001 |

* cited by examiner

*Primary Examiner*—Corrine McDermott
*Assistant Examiner*—William H Matthews
(74) *Attorney, Agent, or Firm*—Squire, Sanders & Dempsey, L.L.P.

(57) ABSTRACT

An implantable prosthesis, for example a stent, is provided having one or more elements that form the body structure of the prosthesis. The elements have a width that is variable from a nominal or conventional width to an increased width. Depots are formed in the elements and are generally located at the increased width portions of the elements. The diameter of the depots is based on a percentage of the width of the element. As such, the depots have increased drug-loading capabilities. Substances such as therapeutic substances, polymeric materials, polymeric materials containing therapeutic substances, radioactive isotopes, and radiopaque materials can be deposited into the depots. Further, the variable width of the elements ensures that sufficient material surrounds each depot so as not to compromise the structural integrity of the prosthesis.

4 Claims, 5 Drawing Sheets

INCREASED DRUG-LOADING AND REDUCED STRESS DRUG DELIVERY DEVICE

FIELD OF THE INVENTION

This invention relates generally to implantable devices, such as expandable intraluminal prosthesis. More particularly, this invention relates to an implantable prosthesis having a plurality of depots formed in the device to deliver fluid to tissues.

BACKGROUND OF THE INVENTION

A variety of surgical procedures and medical devices are currently used to relieve intraluminal constrictions caused by disease or tissue trauma. An example of one such procedure is percutaneous transluminal coronary angioplasty (PTCA). PTCA is a catheter-based technique whereby a balloon catheter is inserted into a blocked or narrowed coronary lumen of the patient. Once the balloon is positioned at the blocked lumen or target site, the balloon is inflated causing dilation of the lumen. The catheter is then removed from the target site thereby allowing blood to freely flow through the unrestricted lumen.

Although PTCA and related procedures aid in alleviating intraluminal constrictions, such constrictions or blockages reoccur in many cases. The cause of these recurring obstructions, termed restenosis, is due to the body's response to the surgical procedure and implant. As a result, the PTCA procedure may need to be repeated to repair the damaged lumen.

Stents or drug therapies, either alone or in combination with the PTCA procedure, are often used to avoid or mitigate the effects of restenosis at the surgical site. In general, stents are small, cylindrical devices whose structure serves to create or maintain an unobstructed opening within a lumen. The stents are typically made of biocompatible alloys and metals, such as stainless steel and Nitinol™, and are delivered to the target site via a catheter. Although the stents are effective in opening the stenotic lumen, the foreign material and structure of the stents themselves may exacerbate the occurrence of restenosis or thrombosis.

Drugs or similar agents that limit or dissolve plaque and clots are used to reduce, or in some cases eliminate, the incidence of restenosis and thrombosis. The term "drug(s)," as used herein, refers to all therapeutic agents, diagnostic agents/reagents and other similar chemical/biological agents, including combinations thereof, used to treat and/or diagnose restenosis, thrombosis and related conditions. Examples of various drugs or agents commonly used include heparin, hirudin, antithrombogenic agents, steroids, ibuprofen, antimicrobials, antibiotics, tissue plasma activators, monoclonal antibodies, and antifibrosis agents.

Since the drugs are applied systemically to the patient, they are absorbed not only by the tissues at the target site, but by all areas of the body. As such, one drawback associated with the systemic application of drugs is that areas of the body not needing treatment are also affected. To provide more site-specific treatment, stents can be used as a means of delivering the drugs exclusively to the target site.

The drugs are stored in a tissue-compatible polymer, such as silicone, polyurethane, polyvinyl alcohol, polyethylene, polyesters, hydrogels, hyaluronate, various copolymers or blended mixtures thereof. The polymer matrix is applied to the surfaces of the stent generally during the manufacture of the stent. By positioning the stent at the target site, the drugs can be applied directly to the area of the lumen requiring therapy or diagnosis.

In addition to the benefit of site-specific treatment, drug-loaded stents also offer longterm treatment and/or diagnostic capabilities. These stents include a biodegradable or absorbable polymer suspension that is saturated with a particular drug. In use, the stent is positioned at the target site and retained at that location either for a predefined period or permanently. The polymer suspension releases the drug into the surrounding tissue at a controlled rate based upon the chemical and/or biological composition of the polymer and drug.

The above-described devices and methods for treatment of restenosis and thrombosis, and other similar conditions not specifically described, offer many advantages to potential users. However, it has been discovered that such devices and methods may be deficient in their current drug-loading and drug-delivery characteristics. In particular, the amount or volume of drug capable of being delivered to the target site may be insufficient due to the limited surface area of the stent.

SUMMARY OF THE INVENTION

In view of the above, it is apparent that there is a need to provide a fluid delivery device offering increased drug loading capabilities for stents and other prosthetic devices. It is also desirable that the drug-delivery device allows fluids to be released at variable and/or independent rates. There is also a need to provide a method of manufacturing such an improved fluid delivery device that is convenient, efficient and cost effective.

In accordance with various aspects of the present invention, an implantable prosthesis, one example of which includes a stent, has a body structure with a hollow bore that extends longitudinally through the body structure. The outer surface of the prosthesis is capable of contacting an inner lumen surface of a passageway. In addition, the body structure of the prosthesis has one or more elements having a width and a thickness. The width of the element(s) is variable from a nominal or conventional width to an increased width.

In another aspect of the present invention, a variable width prosthesis includes one or more depots formed on the elements of the prosthesis. The depots have an open end, a closed end, a diameter and a depth that is less than the thickness of the body structure of the prosthesis. In general, the depots are formed at the increased width sections of the elements. The depots have an increased diameter that improves the drug loading capacity of the prosthesis. The variable width of the prosthesis also gives a wavy appearance to the profile of each element. The wavy appearance of the elements of the prosthesis improves the gripping of the prosthesis onto the delivery system. In addition, the variable width of each element is designed to mesh with the variable width of adjacent elements, thereby optimizing the profile of the prosthesis.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

DETAILED DESCRIPTION OF THE INVENTION

Figure 1:
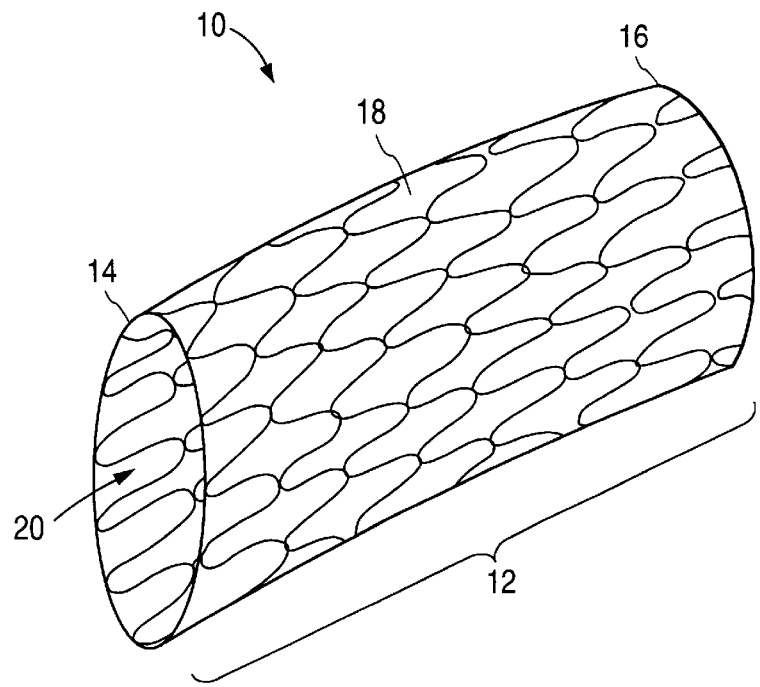
FIG. 1 is a side three-dimensional view of an implantable prosthesis, such as stent, in accordance with an embodiment of the present invention.

FIG. 1 illustrates an implantable prosthetic medical device 10. In the spirit of convenience and brevity, the medical device referenced in the text and figures of the present disclosure is a stent. However, it should be noted that other medical devices or prostheses are also within the scope of the claimed invention.

As shown for example in FIG. 1, the stent 10 is generally cylindrical or tubular in shape or body structure 12 and has a first end 14, a second end 16 and a mid-section 18. In addition, a hollow bore 20 extends longitudinally through the body structure 12 of the stent 10. The structure of the stent 10 allows insertion into an anatomical passageway where the stent 10 physically holds open the anatomical passageway by exerting a radially outward-extending force against the walls or inner lumen surface of the passageway. If desired, the stent 10 can also expand the opening of the lumen to a diameter greater than the lumen's original diameter and, thereby, increase fluid flow through the lumen.

Figure 2:
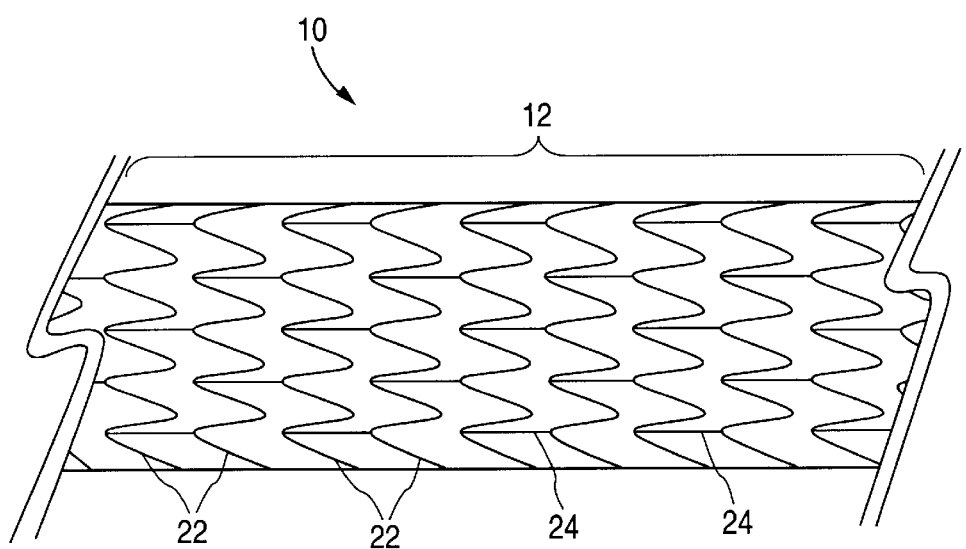
FIG. 2 is a side view showing elongated elements and interconnecting elements that are suitable for usage in an implantable prosthesis in accordance with FIG. 1.
Figure 3:
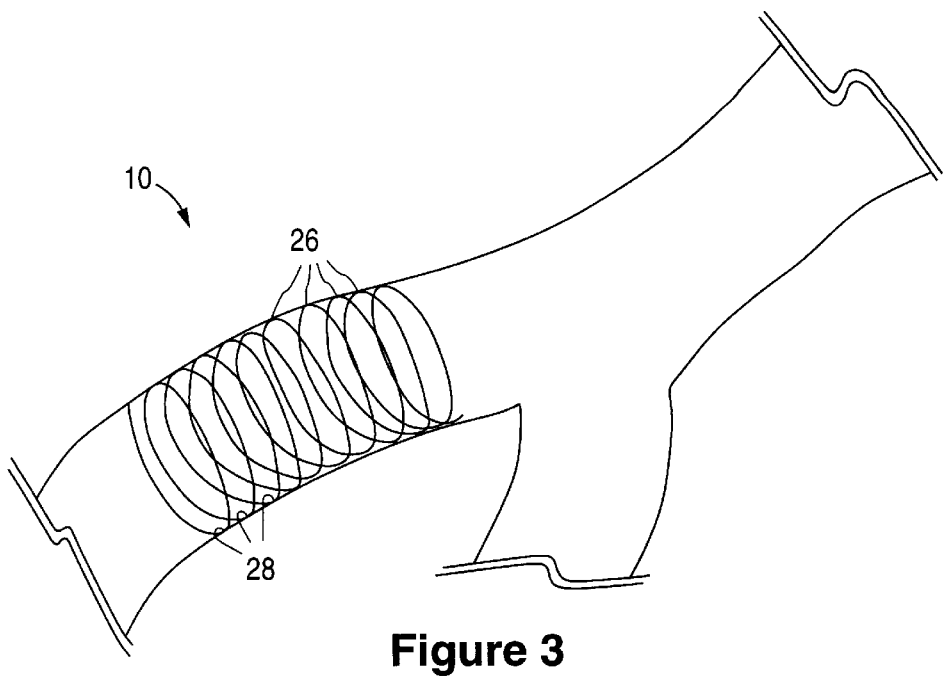
FIG. 3 illustrates an implantable prosthesis inserted into the lumen of a patient.

Referring to FIG. 2, one embodiment of the stent 10 includes one or more resiliently flexible elongated elements 22 that makeup the body 12 of the stent 10. The individual shape of the preformed elongated elements 22 may be straight, sinusoidal, filament type, V-shaped, or any other of a variety of suitable patterns and shapes not disclosed explicitly herein. The elongated elements 22 are radially expandable and interconnected by interconnecting elements 24 that are disposed between adjacent elongated elements 22. As with the elongated elements 22, the interconnecting elements 24 may also have a variety of shapes and patterns including, but not limited to, circular, oval, straight, curved, etc. Both the elongated elements 22 and interconnecting elements 24 define the tubular stent body 12 having a lumen contacting surface 26 and an inner surface 28, as shown in FIG. 3.

Figure 4:
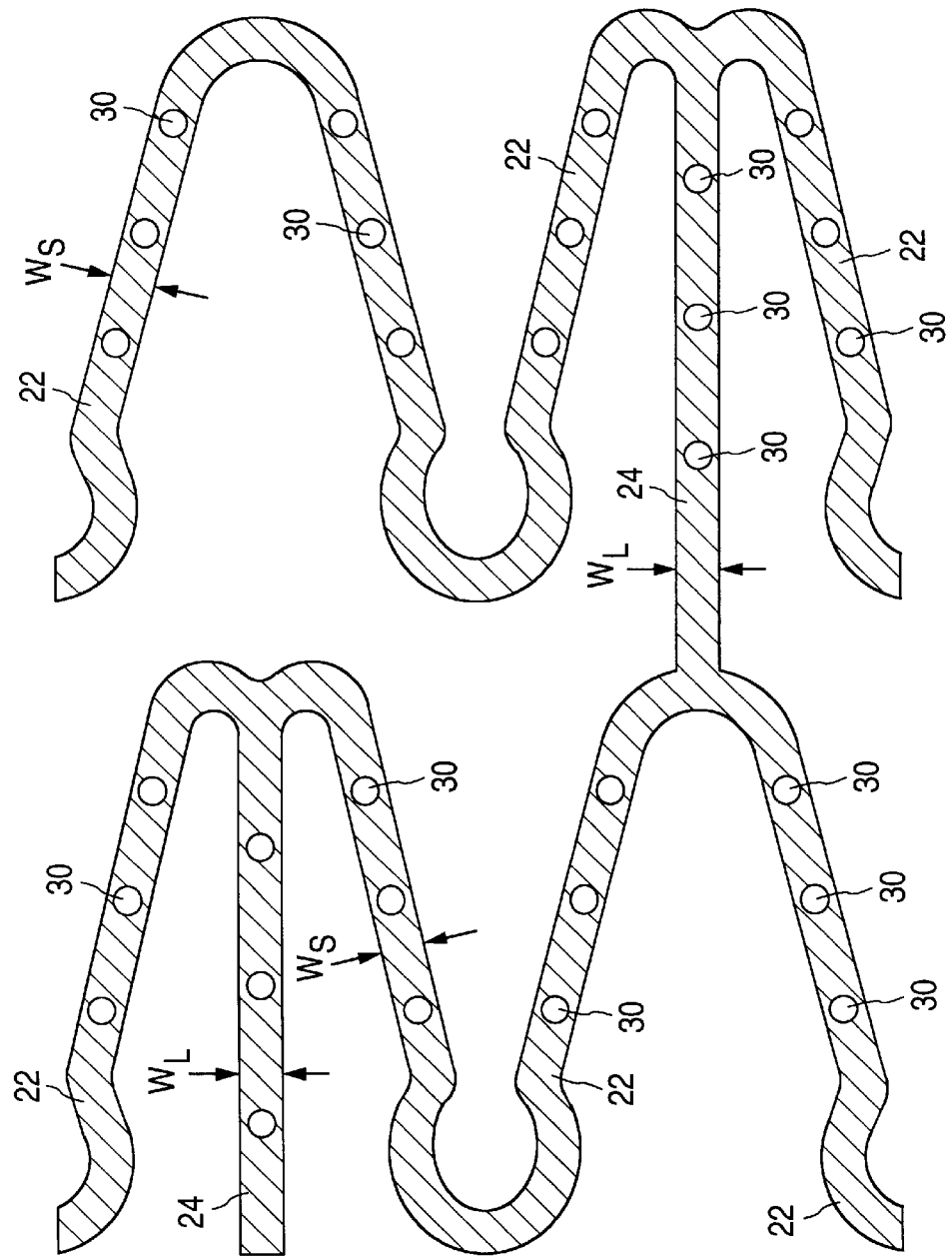
FIG. 4 illustrates a portion of an implantable prosthesis having a plurality of depots on a surface of the prosthesis.

As shown in FIG. 4, the elongated elements 22 and interconnecting elements 24 of the stent 10 have any nominal widths $W_S$ and $W_L$, respectively, typically in a range of widths from about 0.002 inch (0.0051 cm) to about 0.010 inch (0.0254 cm). Additionally, the elongated elements 22 have any suitable thickness (not shown), typically a thickness in a range from about 0.002 inch (0.0051 cm) to about 0.010 inch (0.0254 cm). Similarly, the interconnecting elements 24 also have any nominal thickness (not shown), typically in a range from about 0.002 inch (0.0051 cm) to about 0.010 inch (0.0254 cm). A specific choice of width and thickness depends on the anatomy and size of the target lumen. The size of the stent 10 can vary according to intended procedure, anatomy, and usage.

The elongated elements 22 and interconnecting elements 24 of the stent 10 are configured to allow the stent 10 to easily radially expand and contract, thereby facilitating placement of the stent 10 into an insertion device and, ultimately, a lumen of the body. These components are typically fabricated from biocompatible materials. In one embodiment, the elongated elements 22 and interconnecting elements 24 are fabricated from a metallic material or an alloy such as stainless steel (e.g., 316L), "MP35N," "MP20N," "L605," cobalt, chromium, tantalum, nickeltitanium alloy (commercially available as Nitinol™), platinum-iridium alloy, gold, magnesium, or combinations of alloys. "MP35N" and "MP20N" are trade names for alloys of cobalt, nickel, chromium and molybdenum available from standard Press Steel Co., Jenkintown, Pa. "MP35N" has a nominal composition of 35% cobalt, 35% nickel, 20% chromium, and 10% molybdenum. "MP20N" has a nominal composition of 50% cobalt, 20% nickel, 20% chromium, and 10% molybdenum. The aforementioned list is merely a useful list of materials and that other materials are known by those having skill in the art to function effectively. The particular configuration of the stent 10, including choice of materials, size, structural characteristics, etc., may vary based upon the location and lumen dimensions of the target area.

The stent 10 having one or more depots 30 can be fabricated using several illustrative methods. The methods are applicable to fabricate the stent 10 described hereinbefore and also to fabricate any type of prosthetic device. As shown in FIG. 4, one or more depots or pores 30 are formed on the body 12 of the stent 10 by chemically etching the surface of the stent 10. Alternative methods of forming the depots 30 include laser cutting or ablation techniques, electron beam machining, stamping or electrode discharge machining, including combinations thereof. Furthermore, in addition to perfoming the above-described manufacturing techniques on a prefabricated prosthetic device, such as the stent 10, these same processes can also be used on the individual components or unprocessed materials of the device. For example, with regard to the stent 10, in one embodiment the above-described processes are performed on a flat sheet of material (not shown) from which the elongated elements 22 and interconnecting components 24 are formed. The sheet is fashioned into a cylindrical configuration by securing together opposite ends of the sheet. The ends may be secured together by a variety of techniques including, but not limited to, welding or adhesive bonding.

In an alternate embodiment, the above-described processes are performed on a thin-walled tubular member, such as a hypotube (not shown). The elongated elements 22 and interconnecting components 24 are formed directly on the tubular member. These and other related techniques of fabricating the depots 30 on the stents 10 are well-known to one of ordinary skill in the art. Further, the depots 30 can be formed in virtually any stent structure and not merely the above-described structure.

The depots 30 are formed to carry a variety of substances including, but not limited to, therapeutic substances, polymers impregnated with therapeutic substances, radioactive isotopes, and radiopaque materials. Examples of therapeutic substances or agents used with the present invention include antineoplastics, anti-inflammatory substances, antiplatelets, anticoagulants, fribrinolytics, thrombin inhibitors, antimitotics, and antiproliferatives. Examples of antineoplastics include paclitaxel and docetaxel. Examples of antiplatelets, anticoagulants, fribrinolytics, and thrombin inhibitors include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen, Inc., Cambridge, Mass.), and 7E-3B® (an antiplatelet drug from Centocore, Inc., Malvern, Pa.). Examples of suitable antimitotic agents include methotrexate, azathioprine, vincristine, vinblastine, flurouracil, adriamycin, actinomycin D, and mutamycin. Examples of suitable cytostatic or antiproliferative agents include angiopeptin (a somatostatin analogue from Beaufour Ipsen S.A., Paris, France), angiotensin converting enzyme inhibitors such as Captoprile® (available from Bristol-Myers Squibb Co., New York, N.Y.), Cilazapril® (available from Hoffmann-La Roche Inc., Nutley, N.J.), or Lisinopril® (available from Merck & Co., Inc., Whitehouse Station, N.J.); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck & Co., Inc.), monoclonal antibodies (such as PDGF receptors), nitroprusside, phosphodiesterase inhibitors, prostaglandin inhibitor (available from GlaxoSmithKline plc, Middlesex, United Kingdom), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. In yet other embodiments, the therapeutic substance is a radioactive isotope for stent usage in radiotherapeutic procedures. Examples of radioactive isotopes include, but are not limited to, phosphoric acid ($H_3P^{32}O_4$), palladium ($Pd^{103}$), cesium ($CS^{131}$), and iodine ($I^{125}$). While the listed therapeutic substances or agents are well known for preventative and therapeutic utility, the substances are listed by way of example and are not meant to be limiting. Other therapeutic substances which are currently available or that may be developed in the future are equally applicable. The treatment of patients using the above mentioned medicines is well-known to those of ordinary skill in the art.

The location and configuration of the depots 30 vary according to intended usage and application of the prosthesis. In one embodiment, the depots 30 are evenly distributed throughout the body of the stent 10 and have an equal volume so that tissue in contact with the stent 10 receives an equal distribution of therapeutic substances. In an alternate embodiment, the volume of the depots 30 is greater at each end 14, 16 of the stent 10 compared to the mid-section 18 of the stent 10. For example, in one embodiment, the depots 30 at the ends 14, 16 of the stent 10 carry heparin, whereas the mid-section 18 depots 30 carry methotrexate. Alternate embodiments of the stents 10 having different depot patterns or configurations, volumes and therapies, configured according to clinical purpose and usage requirements, though not specifically described herein, are also included within the scope of the present invention.

Figure 5A:
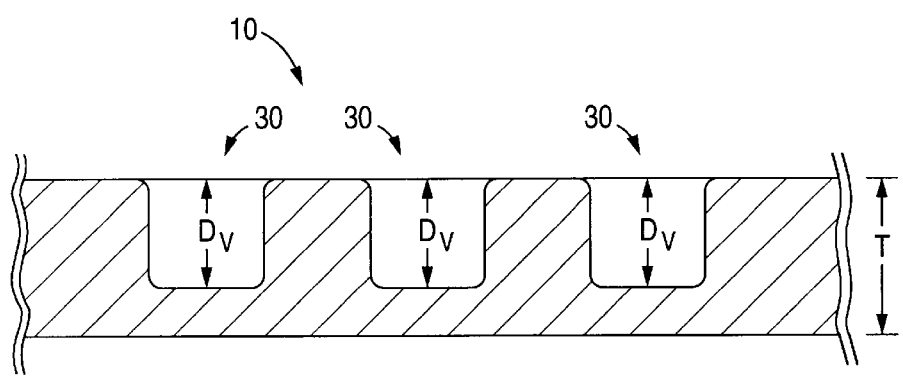
FIG. 5a illustrates a cross-sectional view of a plurality of depots on a surface portion of an implantable prosthesis.
Figure 5B:
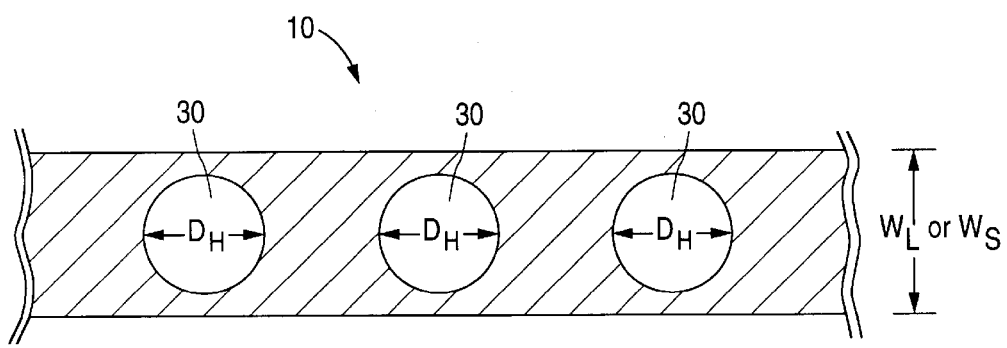
FIG. 5b illustrates a top view of a plurality of depots on a surface portion of an implantable prosthesis.

Referring to FIGS. 5a and 5b, for the stent 10 that carries a therapeutic substance or a polymeric carrier impregnated with a therapeutic substance, a depot or pore depth $D_V$ has a range from about 10% to about 90% of a thickness T. In addition, a depot or pore diameter $D_H$ has a range from about 10% to about 90% of width $W_S$ or $W_L$. The specific depth $D_V$ and diameter DH of the depots 30 depend on the desired amount of therapeutic substance that is to be deposited in the depots 30 and the desired release rates. In an example of a stent 10 that carries a radioactive isotope, the depth $D_V$ is typically about 10% to about 90% of the thickness T and the diameter $D_H$ is typically about 10% to about 90% of the width $W_S$ or $W_L$.

For a stent 10 that carries a radiopaque material, the depot or pore depth $D_V$ has a range from about 10% to about 90% of the thickness T. In addition, the depot or pore diameter $D_H$ has a range from about 10% to about 90% of the width $W_S$ or $W_L$. The depth $D_V$ greater than about 90% of the thickness T and the diameter $D_H$ greater than about 90% of the width $W_S$ or $W_L$ may compromise the structural integrity and mechanical functionality of the stent 10. However, the upper limits of depth $D_V$ and diameter $D_H$ vary depending on the material and design characteristics.

The depth $D_V$ and diameter $D_H$ of the individual depots 30 formed on the stent 10 can vary relative to one another. In one example, depot volume can be selectively controlled along different portions of the stent 10 during stent fabrication, either by selectively varying the volume or making the volume of the depots 30 consistent throughout the body 12 of the stent 10. For some applications, consistent depot volume is important for delivery of a therapeutic substance to insure that the substance is evenly distributed throughout the stent 10 and results in consistent application of the therapeutic substance to the tissues in contact with the surface 26 of the stent 10. Although the depots 30 can be cylindrically shaped with a flat and level bottom, as generally shown in FIG. 5a, alternative depot configurations are also within the scope of the present disclosure. For example, depot configurations, including depot bottoms, can include, but are not limited to, tear-drop shaped, cubic shaped, spherically shaped, and other configurations and shapes not specifically described.

A factor for determining the size, geometry, and concentration of the depots 30 on the stent 10 is the overall stent porosity. Porosity is the total volume of pores in the body 12 of the stent 10 divided by the total volume of structural material (i.e., material having no pores) of the stent 10. Porosity determines the capacity of a substance that can be loaded into the stent 10 of predetermined dimensions. High porosity can adversely affect the structural integrity, strength, and elasticity of the stent 10. Consequently, stent design includes consideration of a tradeoff between strength and stent profile on one hand, and stent load capacity on the other hand.

To increase stent load capacity while maintaining or improving stent strength, the configuration of the stent 10 and the individual depots 30 are modified. In one embodiment, shown in FIGS. 6a and 6b, the diameter of the depots 30 and sections of the widths of the elongated elements 22 and interconnecting elements 24 are increased. Portions of the nominal or conventional widths $W_S$ and $W_L$ are expanded to increased widths $W_S'$ and $W_L'$, respectively, to avoid high stress points around the depots 30 due to insufficient material which can cause breaks or fractures in the stent structure. The increased width $W_S'$ or $W_L'$ is generally within a range from about 0.002 inch (0.0051 cm) to about 0.016 inch (0.0406 cm). In addition, an increased depot or pore diameter $D_H'$ has a range from about 10% to about 90% of increased width $W_L'$ or $W_S'$.

The increased width $W_S'$ or $W_L'$ is limited to those areas of the stent 10 where the depot 30 is located. This, in turn, ensures that the amount of material surrounding the depot 30 remains relatively constant. In general, the edge distances Y and Z, defined as the distances between the outer edge of material surrounding the depot 30 at the increased widths $W_L'$ and $W_S'$, respectively, and the inner edge of material at the depot diameter $D_H'$, are within a range from about 5% to about 45% of the width $W_L'$ or $W_S'$.

Figure 6A:
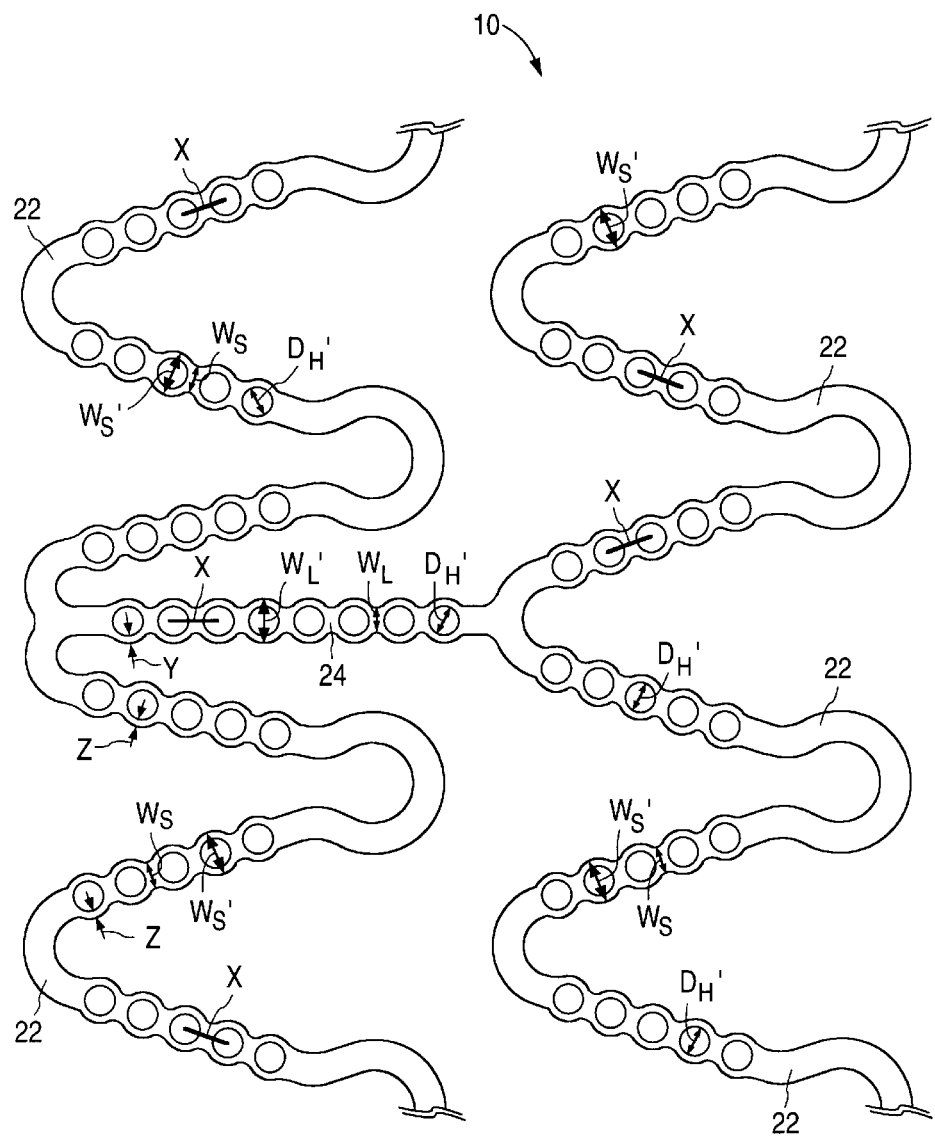
FIGS. 6a and 6b illustrate a portion of an implantable prosthesis having a plurality of depots on a surface of the prosthesis.
Figure 6B:
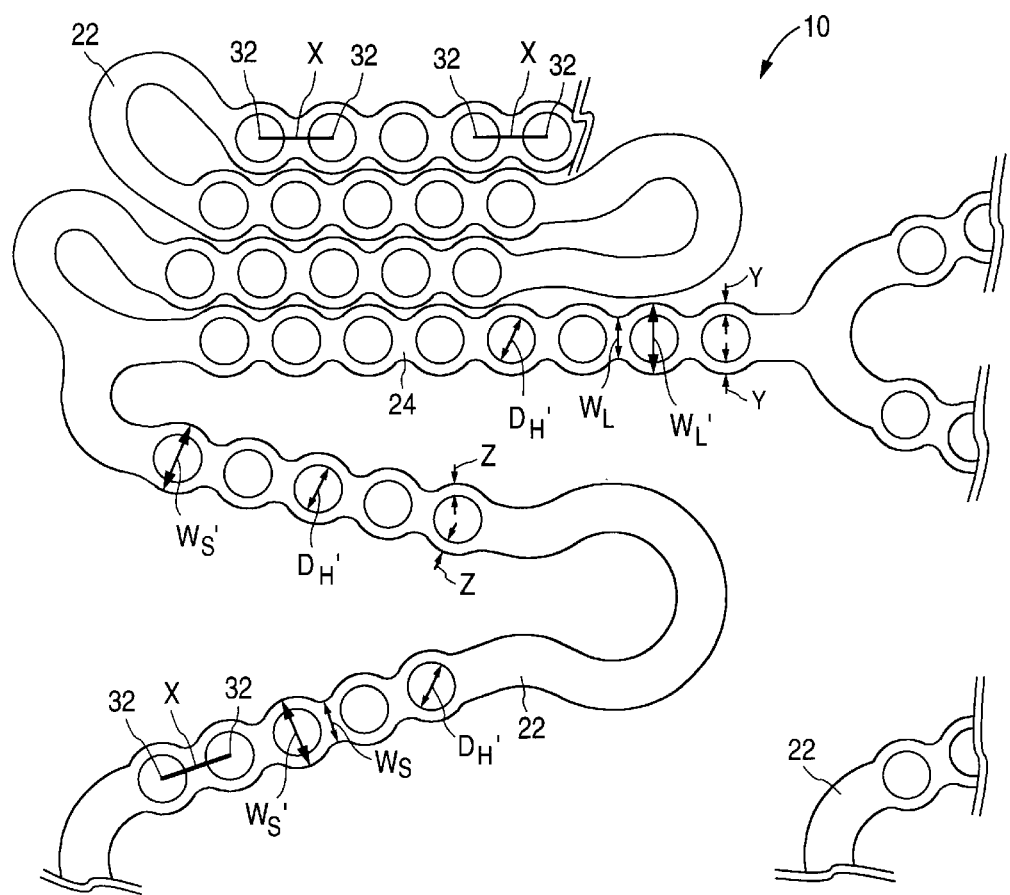

Variable widths along the length of the elongated element 22 and interconnecting elements 24 give a curved, generally sinusoidal or wavy appearance to the profile of these elements. As shown in FIG. 6b, the variable width of each element 22, 24 is designed to match with the variable widths of adjacent elements 22, 24. The interlocking design feature of the elements 22, 24 accommodates both the increased depot diameter and associated width increase, without increasing the overall crimped stent profile. As such, the profile, including both its deployed and compressed states, of the stent 10 having increased depot size and drug loading capacity is generally equivalent to that of a conventional stent profile.

In addition to improving the structural integrity of the stent 10, the increased amount and configuration of material surrounding each depot also enhances stent retention on the delivery system (not shown). For example, the variable widths along the length of the elongated element 22 and interconnecting elements 24 increase the overall surface area of stent material in contact with the surface area of the delivery device. As a result, the amount of friction between these surfaces also increases, thereby forming a secure attachment between the stent 10 and the delivery device. Furthermore, the variable widths also produce a type of gripping action. The wavy or jagged edges of the elongated element 22 and interconnecting elements 24 grip the deployment member, for example the balloon, of the delivery device, preventing slippage or shifting of the stent 10 during the insertion process.

Expanding the depot diameter also significantly improves the drug loading capacity of the stent 10. As an illustration, in general, for a cylindrically shaped depot, a depot area and volume are calculated according to the following formulas:

Depot area=$\pi(D/2)^2$ where $D=D_H$ or $D_H'$

Depot volume=$\pi r^2 h$ where $r=(D_H)/2$ or $(D_H')/2$ and $h=D_V$

An increase in the diameter of the depot 30 has a square effect on the amount of drug capacity. For example, the depot diameter for a conventional stent is approximately 0.004 inch ($1.06 \times 10^{-2}$ cm), resulting in a depot area of approximately $1.256 \times 10^{-5}$ square inch ($8.107 \times 10^{-5}$ square cm). In contrast, the depot area of the stent 10 having an increased depot diameter, for example 0.008 inch ($2.032 \times 10^{-2}$ cm), is approximately $5.024 \times 10^{-5}$ square inch ($3.243 \times 10^{-4}$ square cm). In general, doubling the depot diameter quadruples the amount of drug loading. Furthermore, assuming similar depot depths, the corresponding volume of an increased diameter depot 30 is also greater than the volume of a conventional depot 30 having a conventional diameter. Although the open end of the depot 30 is described and illustratively shown as being circular in form, configurations such as square shaped, triangular, diamond shaped, and other configurations not specifically described herein may also be formed on the prosthesis.

The location and quantity of the depots 30 on the stent 10 vary according to intended usage and application. Moreover, the quantity of the depots 30 located on the elongated elements 22 and interconnecting elements 24 is generally restricted to element size and structural limitations. Typically, a specified quantity of the depots 30 is formed only on the straight segments or portions of the elongated elements 22 and interconnecting elements 24. The curved or bent portions of the elongated elements 22 and interconnecting elements 24 are high stress areas and, therefore, are generally not desirable for depot formation since the depots 30 tend to further compromise the structural integrity of the material at these locations.

However, it has been determined that an increased number of the depots 30 can be formed on the elongated elements 22 and interconnecting elements 24 of the stent 10 provided that the material surrounding each depot 30 is reinforced. As shown in FIGS. 6a and 6b and explained above, modifying the depot design by increasing the amount of material surrounding each depot 30, such that a constant depot edge thickness or distance Y, Z is maintained, provides the required support to preserve the structural integrity of the stent 10 during insertion into the lumen and exposure to blood pressure loading. In addition, a suitable distance X between each depot, whereby distance X is defined as the distance between centerpoints 32 of adjacent depots 30 located on the same element, is at a minimum approximately 50% of the depot diameter $D_H'$. Generally, the number of the depots 30 that can be formed on the elongated element 22 or interconnecting element 24 is variable based upon device design requirements and preferences. Therefore, an increased number of the depots 30, having related increased drug-loading capacity, can be formed on the modified stent design described above.

In addition to modifying drug-loading capacity, depot size also affects drug release rates of the prosthesis or stent 10.

Typically, controlling the size of the opening that contacts the surface of a tissue also controls the rate at which the therapeutic substance is released once the stent 10 is implanted at the desired location of treatment. Increasing the diameter of the depot 30 has a square effect on the overall depot area. As such, an increase in the diameter of the depot opening (i.e., depot area) also corresponds to an increase in the amount of drug loaded in the depot 30, thereby on the stent 10, and the surface contact area between the depot 30 and the tissue target site (not shown). The enlarged depot opening together with the expanded tissue contact area also increases the rate at which the drug is released from the depot 30 and delivered to the target site. Therefore, once loaded, the drug or therapeutic substance remains in the depot 30 until the stent 10 is positioned at the target site and engages the wall of the anatomical passageway. At this point, the drug disseminates from the depots 30 and is absorbed into the tissue of the walls of the passageway that are in contact with the stent 10. Not only are substances swiftly delivered to the tissue at the target site, but also greater volumes of substances are released at the site using the stent 10 of the present invention.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent, comprising:
   a strut having an outer face, an inner face and a pair of first and second side walls extending between the outer face and the inner face, each side wall having an undulated area of alternating concave and convex regions; and
   cavities disposed in the outer face of the strut in the general area where the first and second sidewalls include the convex regions;
   wherein the concave regions of the first side wall are aligned with the concave regions of the second side wall and wherein the convex regions of the first side wall are aligned with the convex regions of the second side wall.

2. The stent of claim 1, wherein the cavities are filled with a substance for a treatment of restenosis.

3. The stent of claim 1, wherein the cavities are filled with a polymeric material containing a therapeutic substance.

4. The stent of claim 1, wherein the cavities have an open end, a closed end, a diameter and a depth.

* * * * *

UNITED STATES PATENT AND TRADEMARK OFFICE
CERTIFICATE OF CORRECTION

PATENT NO. : 6,758,859 B1
DATED : July 6, 2004
INVENTOR(S) : Dang et al.

It is certified that error appears in the above-identified patent and that said Letters Patent is hereby corrected as shown below:

<u>Title page,</u>
Insert Item:
-- [73] Assignee: Advanced Cardiovascular Systems, Inc., Santa Clara, CA (US) --.

Signed and Sealed this

Twenty-first Day of June, 2005

JON W. DUDAS
*Director of the United States Patent and Trademark Office*